(12) United States Patent
Dellaria, Jr.

(10) Patent No.: US 6,207,701 B1
(45) Date of Patent: Mar. 27, 2001

(54) UROKINASE INHIBITORS

(75) Inventor: Joseph F. Dellaria, Jr., Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/493,582

(22) Filed: Jan. 28, 2000

(51) Int. Cl.⁷ .................. A61K 31/38; A61K 31/505; C07D 239/02
(52) U.S. Cl. ............... 514/443; 514/256; 514/257; 514/272; 544/242; 544/222
(58) Field of Search ................ 544/244, 242, 544/224; 514/443, 256, 257, 272

(56) References Cited

U.S. PATENT DOCUMENTS 5,340,833   8/1994   Bridges et al. ............... 514/443

FOREIGN PATENT DOCUMENTS

09493582  * 11/1993  (EP) .

9906361   * 11/1993  (WO) .

* cited by examiner

Primary Examiner—Mukund J. Shah
Assistant Examiner—Sudhaker B. Patel
(74) Attorney, Agent, or Firm—B. Gregory Donner; Gregory W. Steele

(57) ABSTRACT

Compounds having formula I

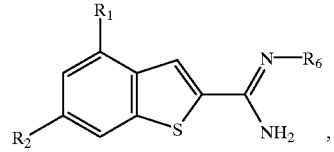

are inhibitors of urokinase and are useful in the treatment of diseases in which urokinase plays a role. Also disclosed are urokinase-inhibiting compositions and a method of inhibiting urokinase in a mammal.

5 Claims, No Drawings

UROKINASE INHIBITORS

TECHNICAL FIELD

The present invention relates substituted benzothiophene compounds which inhibit the urokinase enzyme, pharmaceutical compositions containing these compounds, and medical methods of treatment using these compounds.

BACKGROUND OF THE INVENTION

Urokinase (urinary-type plasminogen activator or uPA (International Union of Biochemistry classification number: EC3.4.21.31)) is a proteolytic enzyme which is highly specific for a single peptide bond in plasminogen. Plasminogen activation (cleavage of this bond by the urokinase enzyme) results in formation of plasmin, a potent general protease.

Many cell types use urokinase as a key initiator of plasmin-mediated proteolytic degradation or modification of extracellular support structures such as extracellular matrix (ECM) and basement membrane (BM). Cells exist, move and interact with each other in tissues and organs within the physical framework provided by ECM and BM. Movement of cells within ECM or across BM requires local proteolytic degradation or modification of the structures and allows cells to invade adjacent areas previously unavailable prior to the degradation or modification.

Cellular invasiveness initiated by urokinase is central to a variety of normal and disease-state physiological processes (Blasi, F., Vassalli, J. D., and Dano, K. J. Cell Biol. 104:801–804, (1987); Dano, K., Anderson, P. A., Grondahl-Hansen, J., Kristensen, P., Nielsen, L. S., and Skriver, L. Adv. Cancer Res. 44:139–266, (1985); Littlefield, B. A. Ann. N. Y. Acad. Sci. 622:167–175, (1991); Saksela, O., Biochim. Biophys. Acta 823:35–65, (1985); Testa, J. E. and Quigley, J. P. Cancer Metast. Rev. 9:353–367, (1990)). Such processes include, but are not limited to, angiogenesis (neovascularization), bone restructuring, embryo implantation in the uterus, infiltration of immune cells into inflammatory sites, ovulation, spermatogenesis, tissue remodelling during wound repair and organ differentiation, fibrosis, tumor invasion, metastatic spread of tumor cells from primary to secondary sites and tissue destruction in arthritis. Amiloride, for example, a known urokinase inhibitor of only moderate potency, has been reported to inhibit tumor metastasis in vivo (Kellen, J. A., Mirakian, A. Kolin, A. Anticancer Res. 8:1373–1376, (1988)) and angiogenesis/capillary network formation in vitro (Alliegro, M. C. and Glaser, B. M. J. Cell Biol. 115[3 Pt 2]: 402a, (1991)).

Inhibitors of urokinase, therefore, have mechanism-based anti-angiogenic, anti-arthritic, anti-inflammatory, anti-retinopathic (for angiogenesis-dependent retinopathies), contraceptive and tumoristatic uses.

SUMMARY OF THE INVENTION

In its principle embodiment, the present invention provides a compound of formula

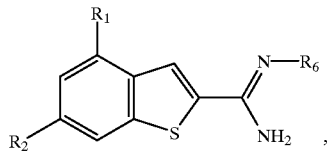

I or a pharmaceutically acceptable salt or prodrug thereof wherein, $R_1$ is selected from hydrogen, and $—NZ_1Z_2$ wherein $Z_1$ and $Z_2$ are independently selected from hydrogen, alkenyl, alkyl, alkynyl, aryl, arylalkyl, heterocycle, and heterocyclealkyl;

$R_2$ is selected from hydrogen, $AOCH_2—$, $AC(O)N(R_3)—$, $AN(R_3)C(O)—$, and

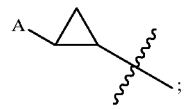

$R_3$ is selected from hydrogen and alkyl;
A is selected from,

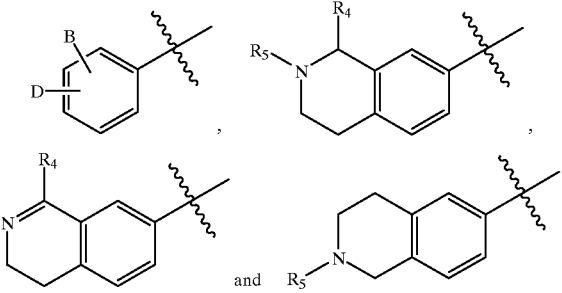

B and D are independently selected from hydrogen, alkenyl, alkoxy, alkoxyalkyl, alkoxycarbonyl, alkyl, alkylcarbonyl, alkylcarbonyloxy, alkynyl, amino, aminocarbonyl, carboxy, cyano, formyl, halogen, haloalkyl, hydroxy, hydroxyalkyl, mercapto, and nitro;

$R_4$ is selected from hydrogen, alkyl, cycloalkyl, cycloalkylalkyl, and optionally substituted aryl;

$R_5$ is selected from hydrogen, alkyl, alkoxycarbonyl, alkylcarbonyl, arylalkyl, arylalkoxycarbonyl, and aminocarbonyl; and $R_6$ is selected from hydrogen and hydroxy;

provided that when $R_1$ is hydrogen, $R_2$ is other than hydrogen.

The present invention also relates to a method of inhibiting urokinase in a mammal, particularly humans, by administering a therapeutically effective amount of a composition comprising a compound of formula (I).

The present invention also relates to pharmaceutical compositions which comprise a therapeutically effective amount of a compound of formula (1) in combination with a pharmaceutically acceptable carrier.

Compounds falling within the scope of formula (I) include, but are not limited to:

4-(2-pyrimidinylamino)-1-benzothiophene-2-carboximidamide, 4-(1,3-thiazol-2-ylamino)-1-benzothiophene-2-carboximidamide, 2-[amino(imino)methyl]-N-phenyl-1-benzothiophene-6-carboxamide, and 2-[amino(imino)methyl]-N-(3-isopropoxyphenyl)-1-benzothiophene-6-carboxamide.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the present invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the present invention, may be made without departing from the spirit and scope thereof.

Definition of Terms

As used throughout this specification and the appended claims, the following terms have the following meanings.

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, tert-butylcarbonyloxy, and the like.

The term "alkynyl," as used herein, refers to a straight or branched chain hydrocarbon group containing from 2 to 10 carbon atoms and containing at least one carbon-carbon triple bond. Representative examples of alkynyl include, but are not limited to, 2-propynyl, 3-butynyl, 2-pentynyl, and the like.

The term "amino," as used herein, refers to $—NR_{20}R_{21}$, wherein $R_{20}$ and $R_{21}$ are independently selected from hydrogen, alkyl, alkylcarbonyl, benzyl, and formyl, as defined herein. Representative examples of amino include, but are not limited to, amino, benzylamino, methylamino, ethylmethylamino, formylamino, methylisopropylamino, dibenzylamino, dimethylamino, diisopropylamino, diethylamino, and the like.

The term "aminoalkyl," as used herein, refers to an amino group, as defined herein, appended to the parent molecular moiety through an alkyl group, as defined herein. Representative examples of aminoalkyl include, but are not limited to, aminomethyl, (benzylamino)methyl, (dimethylamino)methyl, 2-aminoethyl, 3-aminopropyl, 4-amino-1-methylhexyl, and the like.

The term "aminocarbonyl," as used herein, refers to an amino group, as defined herein, appended to the parent molecular moiety through a carbonyl group, as defined herein. Representative examples of aminocarbonyl include, but are not limited to, aminocarbonyl, benzylaminocarbonyl, methylaminocarbonyl, dimethylaminocarbonyl, ethylmethylaminocarbonyl, and the like.

The term "aminocarbonylalkyl," as used herein, refers to an aminocarbonyl group, as defined herein, appended to the parent molecular moiety through an alkyl group, as defined herein. Representative examples of aminocarbonylalkyl include, but are not limited to, methylaminocarbonylmethyl, 2-(methylaminocarbonyl)ethyl, dimethylaminocarbonylmethyl, ethylmethylaminocarbonylmethyl, 2-(ethylmethylaminocarbonyl)ethyl, benzylaminocarbonylmethyl, and the like.

The term "aryl," as used herein, refers to a phenyl group.

The aryl groups of this invention can be substituted with 1, 2, or 3 substituents independently selected from alkenyl, alkoxy, alkoxyalkyl, alkoxycarbonyl, alkyl, alkylcarbonyl, alkylcarbonyloxy, alkynyl, amino, aminocarbonyl, carboxy, cyano, formyl, halogen, haloalkoxy, haloalkyl, hydroxy, hydroxyalkyl, mercapto, and nitro.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and the like.

The term "aryloxy," as used herein, refers to an aryl group, as defined herein, appended to the parent molecular moiety through an oxy moiety, as defined herein. Representative examples of aryloxy include, but are not limited to, phenoxy, 3-bromophenoxy, 4-chlorophenoxy, 4-methylphenoxy, 3,5-dimethoxyphenoxy, and the like.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, 3-carboxypropyl, and the like.

The term "cyano," as used herein, refers to a —CN group.

The term "cycloalkyl," as used herein, refers to a saturated cyclic hydrocarbon group containing from 3 to 8 carbons. Representative examples of cycloalkyl include, but are not limited to, cyclopropyl, cyclobutyl, cyclopentyl, cyclohexyl, cycloheptyl, cyclooctyl and the like.

The term "cycloalkylalkoxy," as used herein, refers to cycloalkyl group, as defined herein, appended to the parent molecular moiety through an alkoxy group, as defined herein. Representative examples of cycloalkylalkoxy include, but are not limited to, cyclopropylmethoxy, 2-cyclobutylethoxy, cyclopentylmethoxy, cyclohexylmethoxy, and the like.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "cycloalkyloxy," as used herein, refers to cycloalkyl group, as defined herein, appended to the parent molecular moiety through an oxy group, as defined herein. Representative examples of cycloalkyloxy include, but are not limited to, cyclopropyloxy, cyclobutyloxy, cyclopentyloxy, cyclohexyloxy, and the like.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, pentafluoroethoxy, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl, thiopyranyl, triazinyl, triazolyl, trithianyl, and the like. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzothiazolyl, benzothiophene, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolyl, phthalazinyl, pyranopyridyl, quinolyl, quinolizinyl, quinoxalinyl, quinazolinyl, tetrahydroisoquinolyl, tetrahydroquinolyl, thiopyranopyridyl, and the like. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzofuranyl, dibenzothienyl, naphthofuranyl, naphthothienyl, oxanthrenyl, phenazinyl, phenoxathiinyl, phenoxazinyl, phenothiazinyl, thianthrenyl, thioxanthenyl, xanthenyl, and the like.

The heterocycles of this invention can be substituted with 1, 2,or 3 substituents independently selected from alkenyl, alkoxy, alkoxyalkyl, alkoxycarbonyl, alkyl, alkylcarbonyl, alkylcarbonyloxy, alkynyl, amino, aminocarbonyl, carboxy, cyano, formyl, halogen, haloalkyl, hydroxy, hydroxyalkyl, mercapto, and nitro.

The term "heterocyclealkyl," as used herein, refers to a heterocycle, as defined herein, appended to the parent molecular moiety through an alkyl group, as defined herein. Representative examples of heterocyclealkyl include, but are not limited to, pyrid-3-ylmethyl, 2-pyrimidin-2-ylpropyl, and the like.

The term "heterocycleoxy," as used herein, refers to a heterocycle group, as defined herein, appended to the parent molecular moiety through an oxy moiety, as defined herein. Representative examples of heterocycleoxy include, but are not limited to, pyrid-3-yloxy, pyrimidin-2-yloxy, quinolin-3-yloxy, thiazol-2-yloxy, and the like.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2-ethyl-4-hydroxyheptyl, and the like.

The term "hydroxy-protecting group" or "O-protecting group," refers to a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsiyl)ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used bydroxy-protecting groups are disclosed in T. H. Greene and P. G. M. Wuts, Protective Groups in Organic Synthesis, 2nd edition, John Wiley & Sons, New York (1991).

The term "lower alkyl," as used herein, refers to a straight or branched chain hydrocarbon group containing from 1-to-4 carbon atoms. Representative examples of lower alkyl include, but are not limited to, methyl, ethyl, n-propyl, iso-propyl, n-butyl, iso-butyl, tert-butyl, and the like.

The term "mercapto," as used herein, refers to a —SH group.

The term "nitro," as used herein, refers to a —NO$_2$ group.

The term "nitrogen protecting group" or "N-protecting group," as used herein, refers to those groups intended to protect an amino group against undesirable reactions during synthetic procedures. N-protecting groups comprise carbamates, amides, N-benzyl derivatives, and sulfonamides. Preferred N-protecting groups are formyl, acetyl, benzoyl, pivaloyl, phenylsulfonyl, benzyl, triphenylmethyl (trityl), t-butoxycarbonyl (Boc), benzyloxycarbonyl (Cbz), and the like. Commonly used N-protecting groups are disclosed in (T. H. Greene and P. G. M. Wuts, Protective Groups in Organic Synthesis, 2nd edition, John Wiley & Sons, New York (1991)).

The term "—NZ$_1$Z$_2$," as used herein, refers to two groups, Z$_1$ and Z$_2$, which are appended to the parent molecular moiety through a nitrogen atom. Z$_1$ and Z$_2$ are independently selected from hydrogen, alkyl, aryl, arylalkyl, heterocycle, and heterocyclealkyl. Representative examples of —NZ$_1$Z$_2$ include, but are not limited to, amino, benzylamino, methylamino, acetylamino, acetylmethylamino, 2-pyrimidinylamino, 1,3-thiazol-2-ylamino, 2-thienylamino, and the like.

The term "oxy," as used herein, refers to a -O- moiety.

In one preferred embodiment, the present invention discloses compounds having formula II:

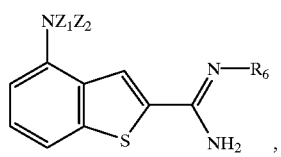

wherein Z$_1$ is heterocycle; Z$_2$ is selected from hydrogen and alkyl; and R$_6$ is as defined in formula I.

In another preferred embodiment, the present invention discloses compounds having formula II wherein Z$_1$ is selected from furyl, imidazolyl, oxadiazolyl, oxazolyl, pyrazinyl, pyrazolyl, pyridyl, pyrimidinyl, pyridazinyl, pyrrolyl, tetrazolyl, thiadiazolyl, thiazolyl, thienyl, and triazolyl; Z$_2$ is selected from hydrogen and alkyl; and R$_6$ is hydrogen.

In another preferred embodiment, the present invention discloses compounds having formula III:

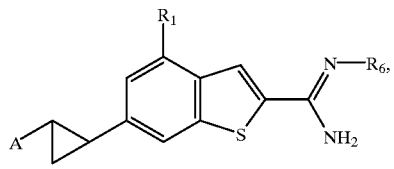

wherein R$_1$, R$_6$ and A are as defined in formula I.

In another preferred embodiment, the present invention discloses compounds having formula III wherein R$_1$ is hydrogen; and R$_6$ and A are as defined in formula I.

In another preferred embodiment, the present invention discloses compounds having formula IV:

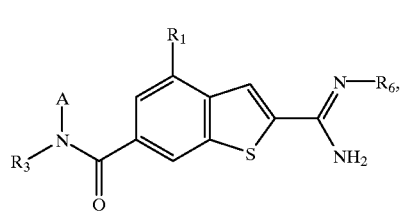

wherein R$_1$, R$_3$, R$_6$, and A are as defined in formula I.

In another preferred embodiment, the present invention discloses compounds having formula IV wherein R$_1$ is hydrogen; and R$_3$, R$_6$, and A are as defined in formula I.

In another preferred embodiment, the present invention discloses compounds having formula V:

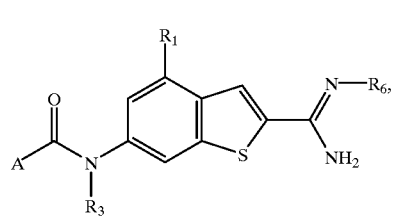

wherein R$_1$, R$_3$, R$_6$, and A are as defined in formula I.

In another preferred embodiment, the present invention discloses compounds having formula V wherein R$_1$ is hydrogen; and R$_3$, R$_6$, and A are as defined in formula I.

In another preferred embodiment, the present invention discloses compounds having formula VI:

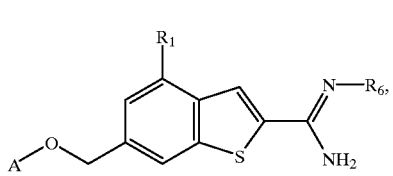

wherein R$_1$, R$_6$, and A are as defined in formula I.

In another preferred embodiment, the present invention discloses compounds having formula VI wherein R$_1$ is hydrogen; and R$_6$ and A are as defined in formula I.

Another preferred embodiment of the present invention relates to pharmaceutical compositions comprising a therapeutically effective amount of a compound of formula I–VI in combination with a pharmaceutically acceptable carrier.

Another preferred embodiment of the present invention relates to a method of inhibiting urokinase in a mammal, particularly humans, comprising administering a therapeutically effective amount of a compound of formula I–VI.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66:1 et seq. The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in (T. Higuchi and V. Stella, Pro-drugs as Novel Delivery Systems, V. 14 of the A.C.S. Symposium Series), and in (Edward B. Roche, ed., Bioreversible Carriers in Drug Design, American Pharmaceutical Association and Pergamon Press (1987)).

The present invention contemplates pharmaceutically active metabolites formed by in vivo biotransformation of compounds of formula I–VI. The term pharmaceutically active metabolite, as used herein, refers to a compound formed by the in vivo biotransformation of compounds of formula I–VI. The present invention contemplates compounds of formula I–VI and metabolites thereof. A thorough discussion of biotransformation is provided in (Goodman and Gilman's, The Pharmacological Basis of Therapeutics, seventh edition, Macmillan, New York, (1985)).

In Vitro Assay

Determination of Urokinase Inhibition

The efficacy of the compounds of this invention as urokinase inhibitors was determined by measuring the inhibition of the urokinase enzyme Abbokinase (Abbott Laboratories, Abbott Park, Ill.) on substrate S-2444, of formula pyroGlu-Arg-pNA-HCl (DiaPharma Group, Inc. Distributor of Chromogenix) at 200 $\mu$M.

The assay was performed in a 96 well polystyrene, flat bottom plate in a 50 mM Tris/0.15 M NaCl+0.5% Pluronic F-68 (Sigma P-5556), pH 7.4 (with HCl) buffer. The compounds of this invention, 10 mM in DMSO, were diluted with DMSO to eight half log concentrations, for example: 1200 $\mu$M, 400 $\mu$M, 120 $\mu$M, 40 $\mu$M, 12 $\mu$M, 4 $\mu$M, 1 $\mu$M and 0.4 $\mu$M. Four concentrations were chosen, then 5 $\mu$l of each were diluted to a total assay volume of 200 $\mu$l. The final compound concentrations in the assay, according to the above example, were 30 $\mu$M, 10 $\mu$M, 3 $\mu$M, 1 $\mu$M, 0.3 $\mu$M, 0.1 $\mu$M, 0.03 $\mu$M and 0.01 $\mu$M, respectively. The substrate S-2444 was used at 200 $\mu$M in the assay. Several vials were reconstituted as directed on the vial, aliquoted and stored frozen. The enzyme was further diluted in assay buffer and 10 $\mu$l was used in the assay. Enzyme concentration in the assay was 2–3 nM. The assay was performed as follows: 175 $\mu$L of buffer was pipetted into the polystyrene plate, 5 $\mu$L solution of a compound of this invention in DMSO was added, the mixture was vortexed, 10 $\mu$L of enzyme in buffer was added, the mixture was vortexed, 10 $\mu$L of substrate in water was added, the mixture was vortexed, and the plate was placed in a Spectromax® (Molecular Devices Corporation, Sunnyvale, Calif.) plate reader to follow the course of the reaction for 15 minutes at 405 nm. The Spectromax® calculated the reaction rates which were used to calculate percent inhibition of the compounds of this invention versus the reaction rate of the enzyme in the absence of any inhibitor. The Ki's of the inhibitors were calculated from the percent inhibition and previously established Km. The compounds of this invention inhibit urokinase as shown by the data for representative Examples in Table 1.

TABLE 1

Inhibitory Potency of Representative Compounds Against Urokinase

| Example | IC$_{50}$ nM |
| --- | --- |
| 1 | 122 |
| 2 | 192 |
| 3 | 3220 |
| 4 | 680 |

As shown by the data in Tables 1, the compounds of this invention inhibit the urokinase enzyme and therefore may have utility in the treatment of diseases prevented by or ameliorated with inhibition of the urokinase enzyme.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. Further included within the scope of the present invention are pharmaceutical compositions comprising one or more of the compounds of formula I–VI prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar—agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) bumectants such as glycerol; d) disintegrating agents such as agar—agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Compounds of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N. Y., (1976), p 33 et seq.

The compounds of the present invention, including but not limited to those specified in the examples, inhibit urokinase. As urokinase inhibitors, the compounds of the present invention may be useful for the treatment of angiogenesis (neovascularization), bone restructuring, embryo implantation in the uterus, infiltration of immune cells into inflammatory sites, ovulation, spermatogenesis, tissue remodelling during wound repair and organ differentiation, fibrosis, tumor invasion, metastatic spread of tumor cells from primary to secondary sites and tissue destruction in arthritis.

When used in the above or other treatments, a therapeutically effective amount of one of the compounds of the present invention can be employed in pure form or, where such forms exist, in pharmaceutically acceptable salt or prodrug form. Alternatively, the compound can be administered as a pharmaceutical composition containing the compound of interest in combination with one or more pharmaceutically acceptable excipients. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, more preferable doses can be in the range of from about 0.01 to about 5 mg/kg/day. If desired, the effective daily dose can be divided into multiple doses for purposes of administration, e.g. two to four separate doses per day.

Abbreviations

The following abbreviations are used: Bu for butyl, dba for dibenzylideneacetone, boc for t-butoxycarbonyl, DBU for 1,8-diazabicyclo[5.4.0]undec-7-ene, DEAD for diethyl azodicarboxylate, DMF for N,N-dimethylformamide, DMSO for dimethyl sulfoxide, DIBAL for diisobutylaluminum hydride, DPPA for diphenylphosphoryl azide, dppf for 1,1'-bis(diphenylphosphino)ferrocene, LDA for lithium diisopropylamide, Me for methyl, NaHMDS for sodium bis(trimethylsilyl)amide, psi for pounds per square inch, p-TsOH for para-toluenesulfonic acid, TEA for triethylamine, TEMP for 2,2,6,6-tetramethylpiperdine, tf for triflic, TLC for Thin Layer Chromatography, THF for tetrahydrofuran, TMSCl for chlorotrimethylsilane.

Preparation of Compounds of the Present Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–14.

Scheme 1

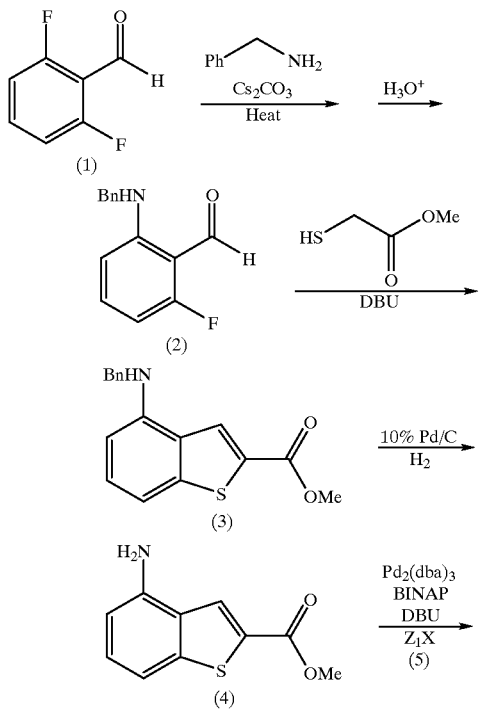

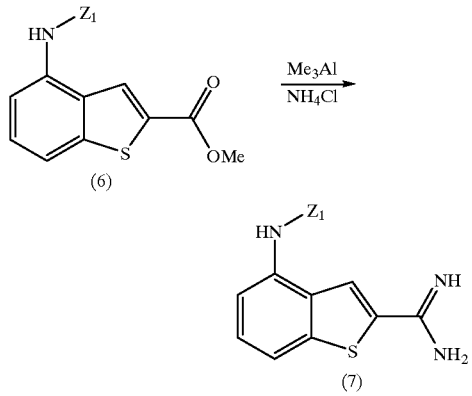

Amidines of general formula (7), wherein $Z_1$ is heterocycle, can be prepared as described in Scheme 1. Commercially available 2,6-difluorobenzaldehyde can be treated with benzylamine and then aqueous acid to provide amino benzaldehyde (2). Amino benzaldehyde (2) can be treated with methyl thioglycolate to provide benzothiophene (3). The benzyl group can be removed using palladium on carbon under a hydrogen atmosphere to provide 4-amino benzothiophene (4). 4-Amino benzothiophene (4) can be treated with BINAP, $Pd_2(dba)_3$, and a heterocyclic halide (5), wherein X is Cl, Br, or I, as described in (Wagaw, S.; Buchwald, S., JOC (1996) 61, 7240–1) to provide benzothiophenes of general formula (6). Benzothiophenes of general formula (6) can be treated with trimethylaluminum and ammonium chloride as described in (U.S. Pat. No. 5,340,833) to provide amidines of general formula (7).

Scheme 2

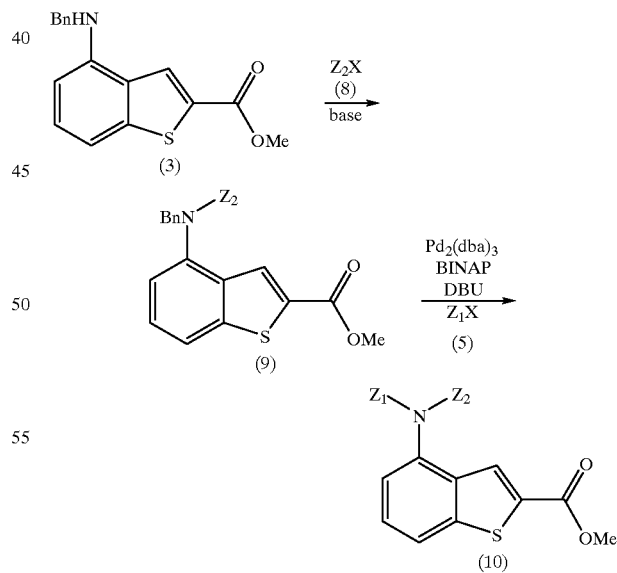

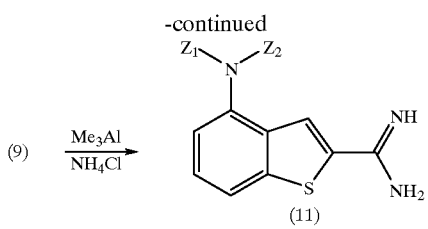

Amidines of general formula (11), wherein $Z_1$ is heterocycle and $Z_2$ is selected from alkenyl, alkyl, and alkynyl, can be prepared as described in Scheme 2. Benzothiophene (3), from Scheme 1, can be treated with a base and halo compounds of general formula (8), wherein X is Cl, Br, or I and $Z_2$ is alkenyl, alkyl, or alkynyl, to provide benzothiophenes of general formula (9). Benzothiophenes of general formula (9) can be processed as described in Scheme 1 to provide benzothiophenes of general formula (10). Benzothiophenes of general formula (10) can be processed as described in Scheme 1 to provide amidine benzothiophenes of general formula (11).

Scheme 3

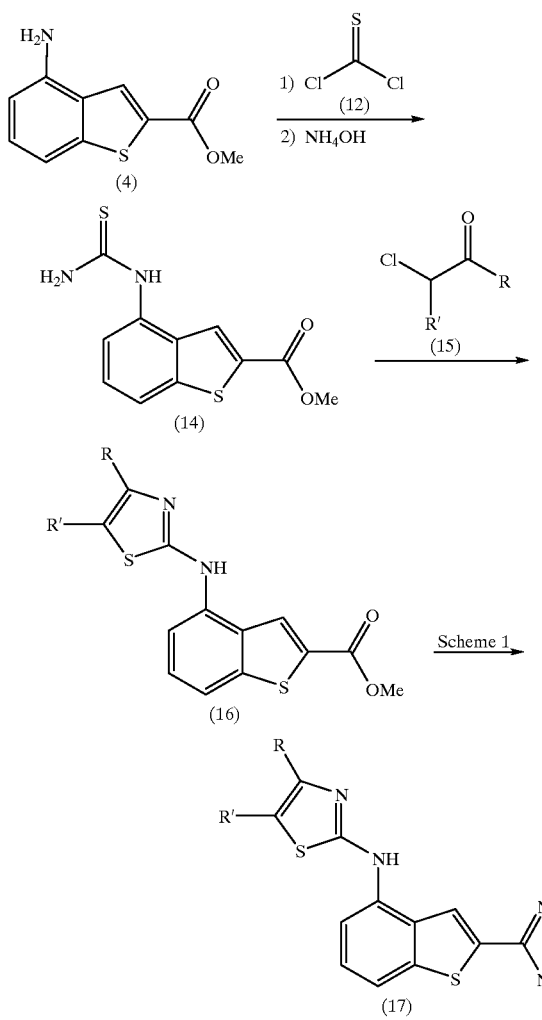

Amidines of general formula (17), wherein R and R' are independently selected from hydrogen and lower alkyl, can be prepared as described in Scheme 3. 4-Amino benzothiophene (4), from Scheme 1, can be treated with thiophosgene to provide the thiourea (14). Thiourea (14) can be treated with alpha-chlorocarbonyls of general formula (15) to provide optionally substituted amino thiazoles (16) which can then be processed as described in Scheme 1 to provide benzothiophenes of general formula (17).

Scheme 4

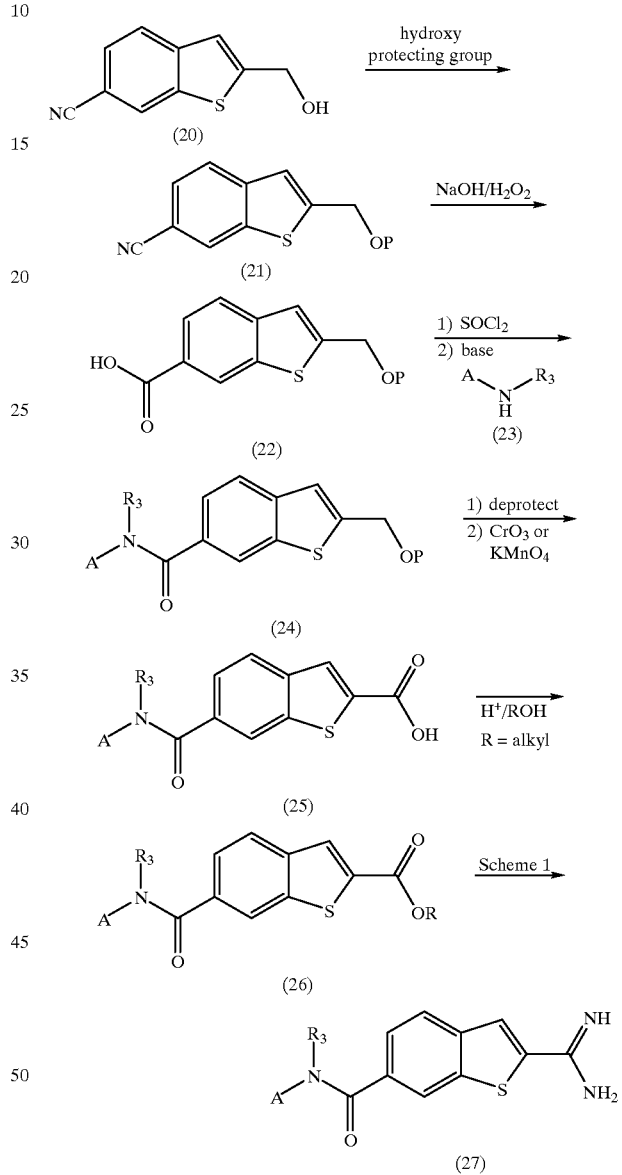

Amidines of general formula (27), wherein A and $R_3$ are as defined in formula I, can be prepared as described in Scheme 4. 6-Cyano 2-(hydroxymethyl)-1-benzothiophene 20), prepared as described in (Dann, O., et al, Liebigs. Ann. Chem., N3 (1986) 438–455), an be O-protected with an appropriate protecting group using conditions and reagents as described in (T. H. Greene and P. G. M. Wuts, Protective Groups in Organic Synthesis, 2nd edition, John Wiley & Sons, New York (1991)) to provide O-protected benzothiophenes of general formula (21). The cyano group can then be converted into a carboxylic acid under standard conditions, such as aqueous $NaOH/H_2O_2$, to provide benzothiophenes of general formula (22). Benzothiophenes of general formula (22) can be converted into acid chlorides using known reagents, such as thionyl chloride or oxalyl chloride/DMF, and then treated with amines of general formula (23), from Schemes 11–13, in the presence of a base to provide 6-amidino benzothiophenes of general formula (24). 6-Amidino benzothiophenes of general formula (24), following deprotection, can be oxidized to 2-carboxy benzothiophenes of general formula (25) using oxidizing agents such as chromic acid or permanganate. The acids of general formula (25) can be treated with HCl and an alcohol, such as methanol, to provide esters of general formula (26), wherein R is alkyl. Esters of general formula (26) can then be processed as described in Scheme 1 to provide amidines of general formula (27).

An alternate method for preparing amidines of general formula (27) can be accomplished by oxidizing compounds of general formula (24), following deprotection of the primary alcohol, to 2-carboxaldehyde benzothiophenes with reagents such as oxalyl chloride/DMSO/TEA (Swern). The 2-carboxaldehyde benzothiophenes can be treated with ozone in an alcohol solvent to provide esters of general formula (26) as described in (Sundararaman, et al.; Tetrahedron Letters (1982) 23, 35). The esters (26) can then be processed as described in Scheme 1 to provide amidines of general formula (27).

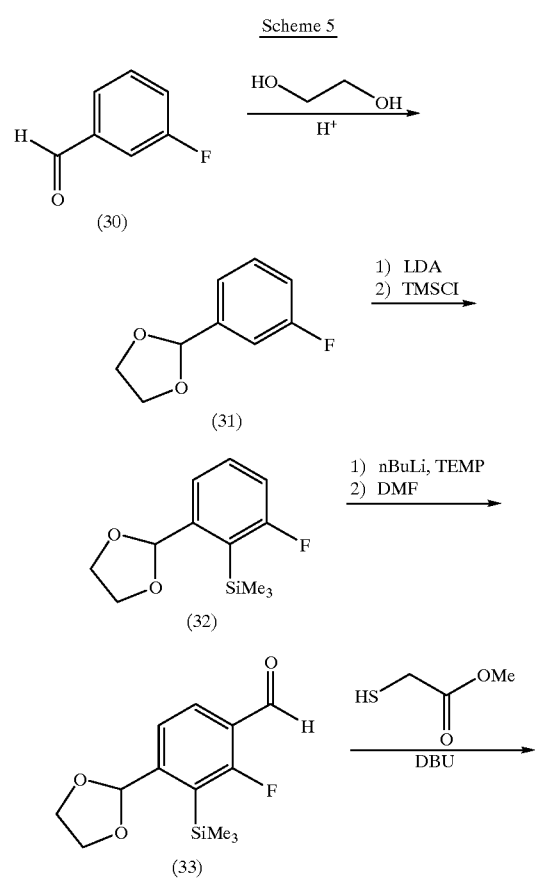

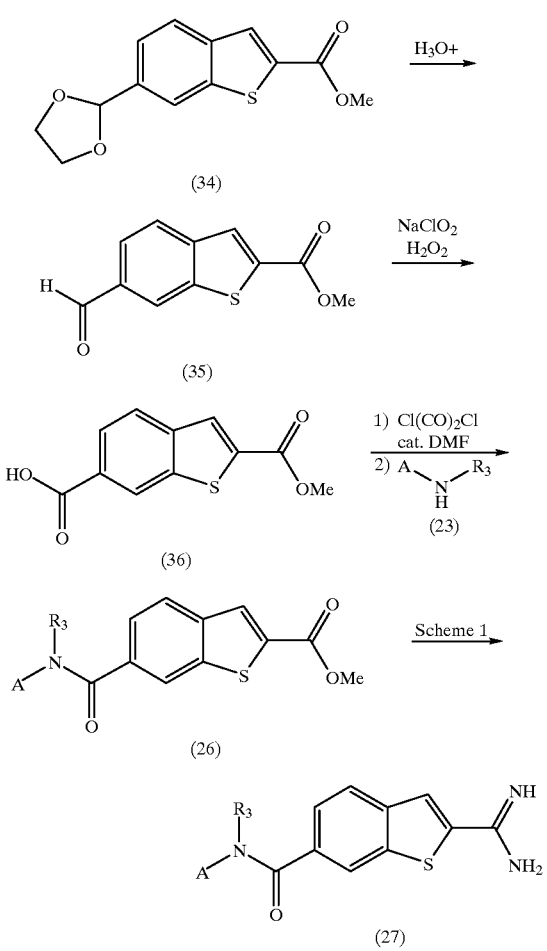

An alternative method for preparing amidines of general formula (27), wherein A and $R_3$ are as defined in formula I, is described in Scheme 5. Commercially available 3-fluorobenzaldehyde (30) can be treated with ethylene glycol and a organic acid such as p-toluenesulfonic acid to provide acetal (31). The acetal (31) can be treated with lithium diisopropylamide followed by trimethylsilyl chloride to provide a silyl benzene (32). The silyl benzene can be treated with n-butyllithium and 2,2,6,6-tetramethylpiperdine to generate an anion which can be quenched with N,N-dimethylformamide to provide benzaldehyde (33). Benzaldehyde (33) can be treated with methyl thioglycolate and DBU to provide benzothiophene (34) which can be hydrolized with an acid such as p-toluenesulfonic acid in acetone to provide benzothiophene (35). Benzothiophene (35) can be treated with sodium chlorite and hydrogen peroxide to provide benzothiophene (36). Benzothiophene (36) can be converted into an acid chloride (thionyl chloride or oxalyl chloride/DMF) and treated with an amine of general formula (23), from Schemes 11–13, to provide benzothiophenes of general formula (26). Benzothiophenes of general formula (26) can be processed as described in Scheme 1 to provide amidines of general formula (27).

Scheme 6

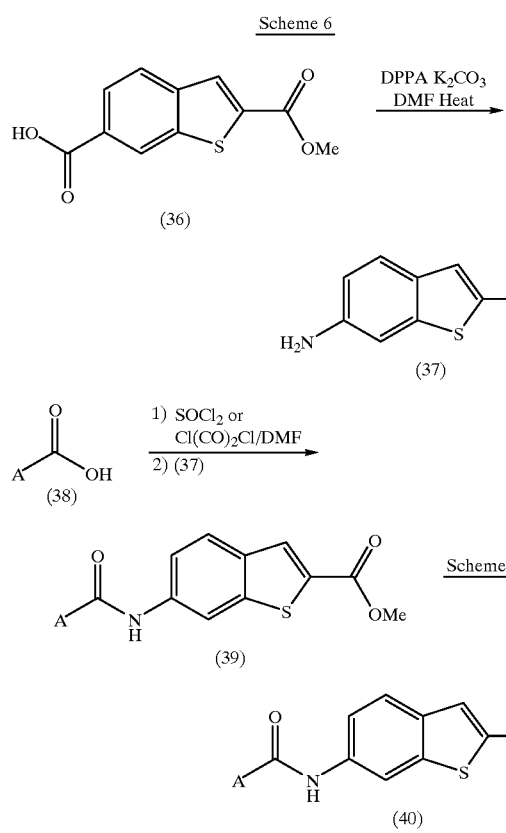

Amidines of general formula (40), wherein A is as defined in formula I, can be prepared as described in Scheme 6. Benzothiophene (36) from Scheme 5 can be treated under Curtius conditions as desribed in (Haefliger, W. and Kloppner, E.; Helv. 65 (1982) 1837) or Schmidt conditions with hydrazoic acid as described in (Palmere, R. and Conley, R.; JOC 35 (1970) 2703) to provide 6-amino benzothiophene (37). Benzothiophene (37) can be acylated with acid chlorides prepared from acids of general formula (38), from Schemes 11–13, to provide benzothiophenes of general formula (39). Benzothiophenes of general formula (39) can be processed as described in Scheme 1 to provide amidines of general formula (40).

Scheme 7

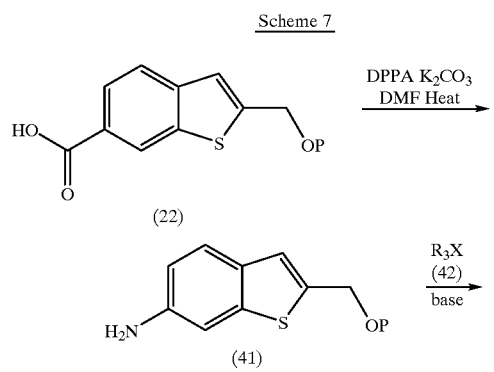

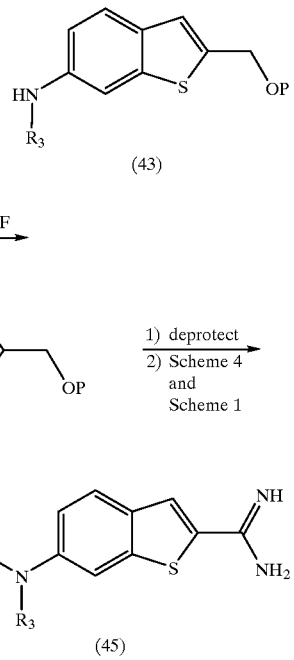

Amidines of general formula (45), wherein $R_3$ is alkyl, can be prepared as described in Scheme 7. Benzothiophene (22), from Scheme 4, can be treated under Curtius conditions as desribed in (Haefliger, W. and Kloppner, E.; Helv. 65 (1982) 1837) or Schmidt conditions with hydrazoic acid as described in (Palmere, R. and Conley, R.; JOC 35 (1970) 2703) to provide 6-amino benzothiophene (41). 6-Amino benzothiophene (41) can be treated with a base such as lithium diisopropylamide and an alkyl halide of general formula (42), wherein X is Cl, Br, or I, to provide 6-amino benothiophenes of general formula (43). Benzothiophenes of general formula (43) can be acylated with acid chlorides prepared from acids of general formula (38), from Schemes 11–13, to provide amides of general formula (44). Amides of general formula (44) can be processed, following deprotection, as desribed in Scheme 4 and Scheme I to provide amidines of general formula (45).

Scheme 8

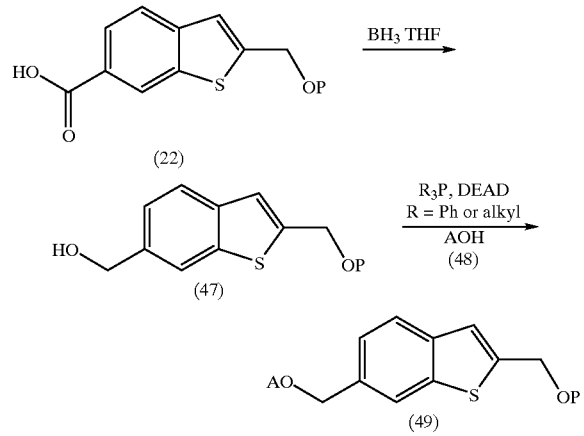

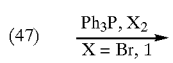

-continued be treated with compounds of general formula (51) to provide ethers of general formula (49). Ethers of general formula (49) can be processed as described in Scheme 4 and Scheme 1 to provide amidines of general formula (53).

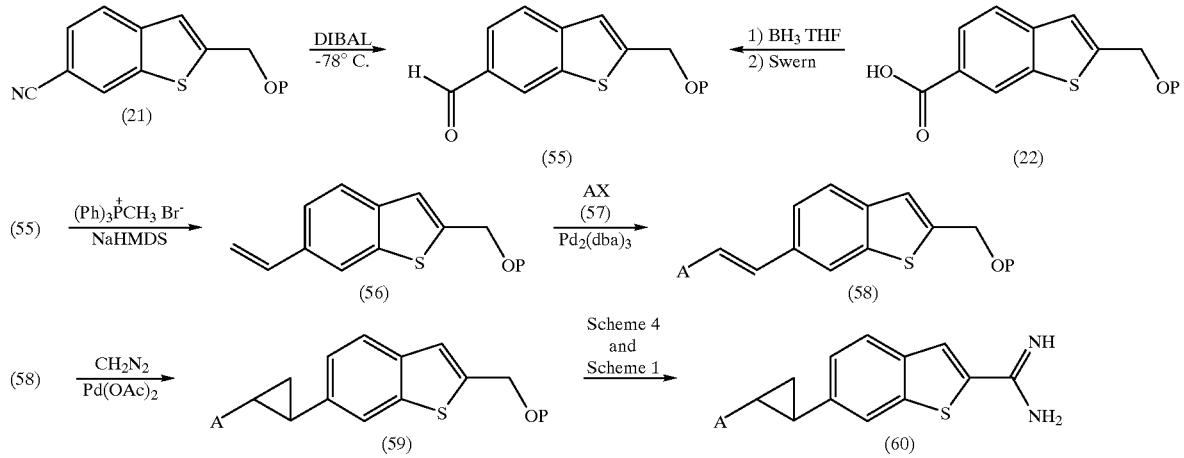

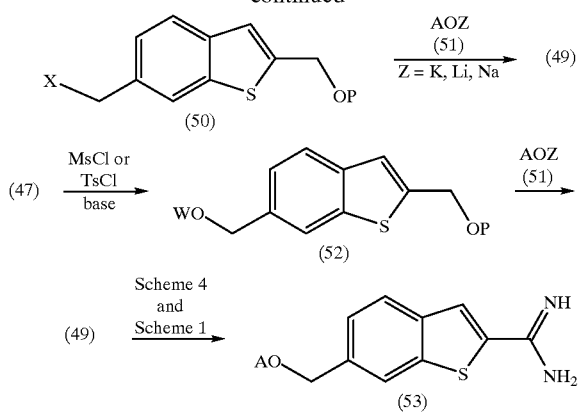

Amidines of general formula (53), wherein A is as defined in formula I, can be prepared as described in Scheme 8. Benzothiophenes of general formula (22), from Scheme 4, can be treated with diborane or a borane-complex to provide alcohols of general formula (47). Alcohols of general formula (47) can be subjected to Mitsunobo conditions in the presence of phenols of general formula (48), from Schemes 11–13, wherein A is as defined in formula I, to provide ethers of general formula (49). Alternatively, alcohols of general formula (47) can be converted into bromides or iodides of general formula (50) using a variety of known conditions/reagents including triphenylphosphine/bromine or triphenylphosphine/iodine. Halides of general formula (50) can be treated with compounds of general formula (51) to provide ethers of general formula (49). Alternatively, alcohols of general formula (47) can be treated with methanesulfonyl chloride or p-toluenesulfonyl chloride in the presence of a base such as triethylamine to provide sulfonates of general formula (52), wherein W is $CH_3S(O)_2$— or $p$-$CH_3C_6H_4S(O)_2$—. Sulfonates of general formula (52) can Amidines of general formula (60), wherein A is as defined in formula 1, can be prepared as described in Scheme 9. Aldehydes of general formula (55) can be prepared by treating cyano benzothiophenes of general formula (21) from Scheme 4 with DIBAL to provide aldehydes (55). Alternatively, carboxy benzothiophenes of general formula (22) from Scheme 4 can be treated with reducing agents such as diborane or a borane-complex to provide primary alcohols which can then be oxidized to aldehydes (55) under Swern conditions. Aldehydes of general formula (55) can be treated with triphenylmethylphosphonium bromide and a base such as NaHMDS to provide terminal olefins of general formula (56). Alkenes of general formula (56) can be treated with compounds of general formula (57), from Schemes 11–13, wherein X is I, Br, $OS(O)_2CF_3$, or $N_2^+BF_4^-$, and a palladium catalyst to provide olefins of general formula (58). Alkenes of general formula (58) can be treated with diazomethane and a palladium catalyst to provide cyclopropyl compounds of general formula (59). Cyclopropanation of olefins of general formula (58) can also be accomplished with diiodomethane, Zn dust, and copper(I) chloride as described in (Simmons and Smith, JACS (1959) 81, 4256; Shank and Shechter, JOC (1959) 24, 1525; LeGoff, JOC (1964)29, 2048). Cyclopropyl compounds of general formula (59) can be processed as described in Scheme 4 and Scheme 1 to provide amidines of general formula (60).

Scheme 10

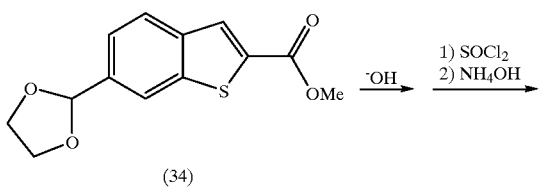

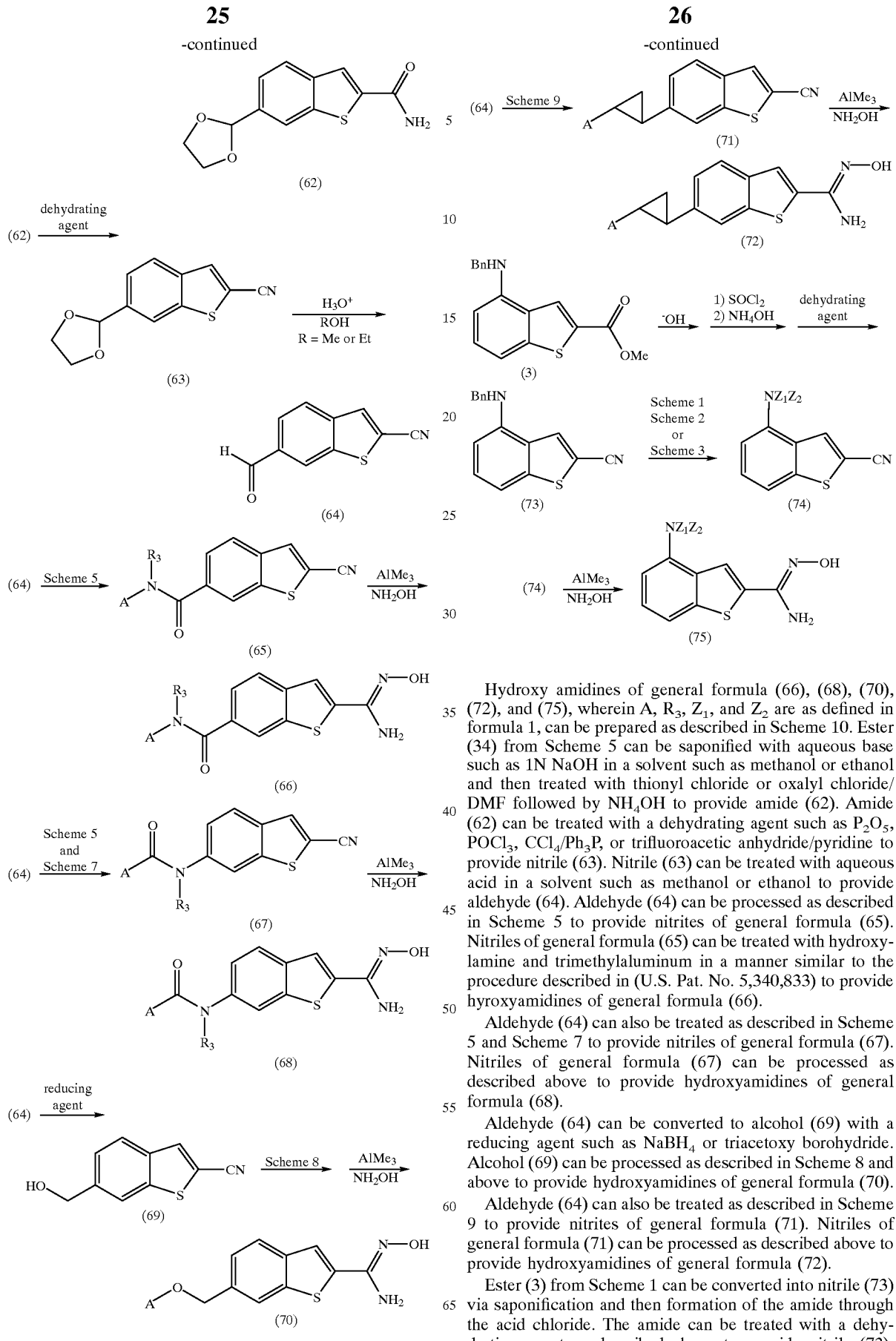

Hydroxy amidines of general formula (66), (68), (70), (72), and (75), wherein A, $R_3$, $Z_1$, and $Z_2$ are as defined in formula 1, can be prepared as described in Scheme 10. Ester (34) from Scheme 5 can be saponified with aqueous base such as 1N NaOH in a solvent such as methanol or ethanol and then treated with thionyl chloride or oxalyl chloride/ DMF followed by $NH_4OH$ to provide amide (62). Amide (62) can be treated with a dehydrating agent such as $P_2O_5$, $POCl_3$, $CCl_4/Ph_3P$, or trifluoroacetic anhydride/pyridine to provide nitrile (63). Nitrile (63) can be treated with aqueous acid in a solvent such as methanol or ethanol to provide aldehyde (64). Aldehyde (64) can be processed as described in Scheme 5 to provide nitriles of general formula (65). Nitriles of general formula (65) can be treated with hydroxylamine and trimethylaluminum in a manner similar to the procedure described in (U.S. Pat. No. 5,340,833) to provide hyroxyamidines of general formula (66).

Aldehyde (64) can also be treated as described in Scheme 5 and Scheme 7 to provide nitriles of general formula (67). Nitriles of general formula (67) can be processed as described above to provide hydroxyamidines of general formula (68).

Aldehyde (64) can be converted to alcohol (69) with a reducing agent such as $NaBH_4$ or triacetoxy borohydride. Alcohol (69) can be processed as described in Scheme 8 and above to provide hydroxyamidines of general formula (70).

Aldehyde (64) can also be treated as described in Scheme 9 to provide nitrites of general formula (71). Nitriles of general formula (71) can be processed as described above to provide hydroxyamidines of general formula (72).

Ester (3) from Scheme 1 can be converted into nitrile (73) via saponification and then formation of the amide through the acid chloride. The amide can be treated with a dehydrating agent as described above to provide nitrile (73).

Nitrile (73) can be processed as described in Scheme 1, Scheme 2, or Scheme 3 to provide nitriles of general formula (74). Nitriles of general formula (74) can be treated with hydroxylamine and trimethylaluminum in a manner similar to the procedure described in (U.S. Pat. No. 5,340,833) to provide hyroxyamidines of general formula (75).

Scheme 11

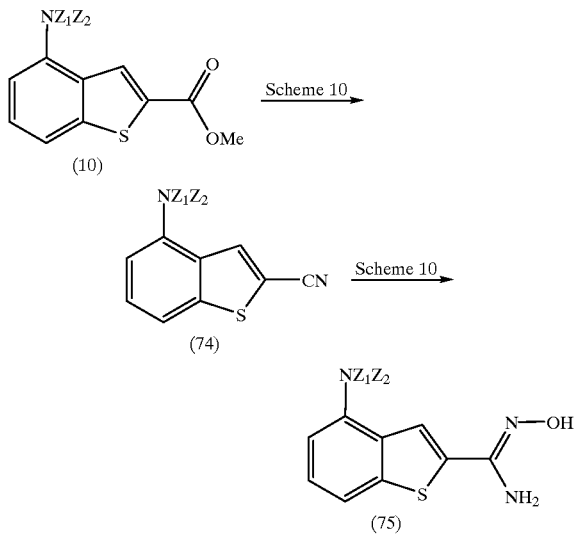

An alternate method of preparing hydroxy amidines of general formula (75), wherein $Z_1$ and $Z_2$ are as defined in formula 1, can be used as described in Scheme 11. Esters of general formula (10), from Scheme 2, can be processed as described in Scheme 10 to provide nitriles of general formula (74). The nitriles can then be processed as described in Scheme 10 to provide hydroxy amidines of general formula (75). Other esters that can be processed as described in Scheme 10 include esters of general formula (6), from Scheme 1, and esters of general formula (16), from Scheme 3.

Scheme 12

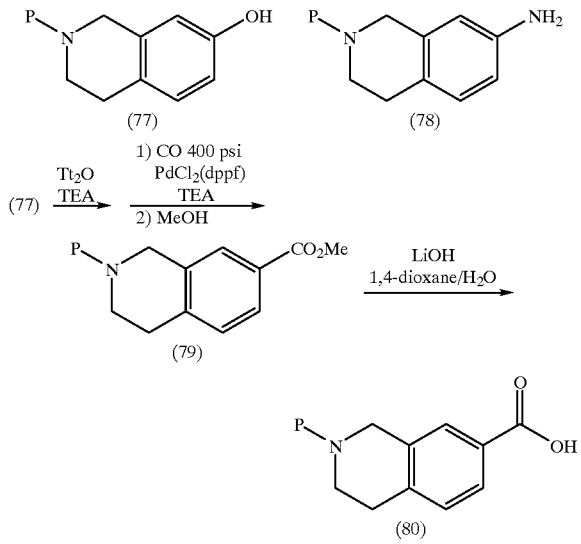

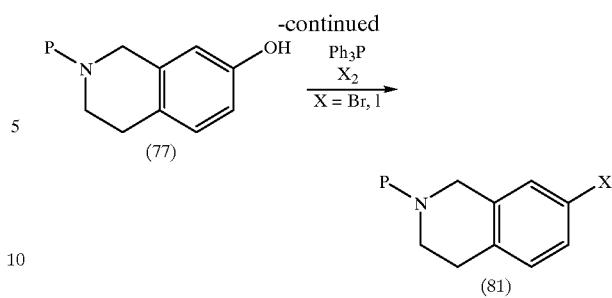

7-Substituted isoquinolines can be prepared as described in Scheme 12. Tetrahydroisoquinolines (77) and (78), wherein P is acetyl, can be prepared as described in (Ajao, J. F. and Bird, C. W., J. Het. Chem. (1985) 329–331). Tetrahydroisoquinoline (77) can be converted to methyl ester (79) via the triflate under conditions of carbon monoxide at 400 psi in the presence of a palladium catalyst in methanol. Methyl ester (79) can be treated with lithium hydroxide in a cosolvent of 1,4-dioxane and water to provide acid (80). Tetrahydroisoquinoline (77) can also be treated with a variety of halogenating reagents/systems such as triphenylphosphine/$Br_2$ or triphenylphosphine/$I_2$ to provide halogens (81), wherein X is Br or I. An alternative method of preparing iodide (81) can be used by converting tetrahydroisoquinoline (77) to the triflate and then treating the triflate with magnesium iodide as described in (Martinez, G., et. al., Synthesis, (1986) N 3, 222–224).

Scheme 13

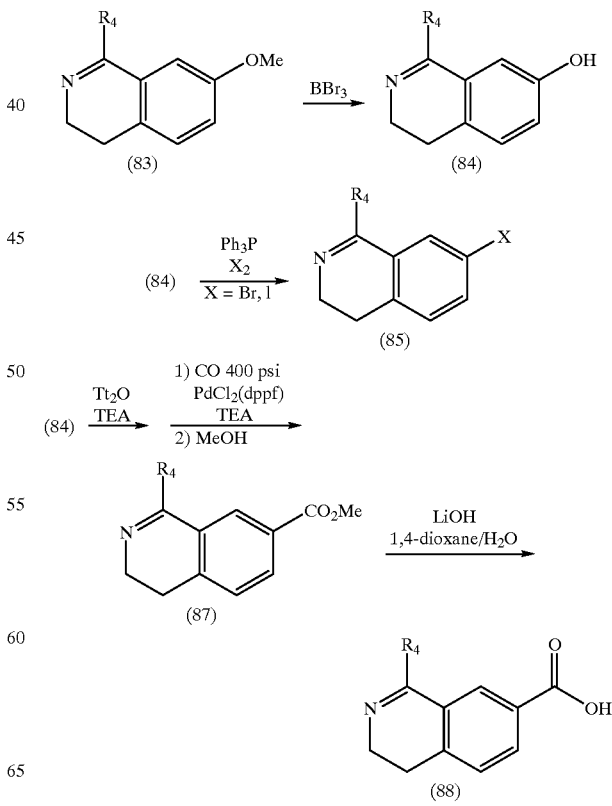

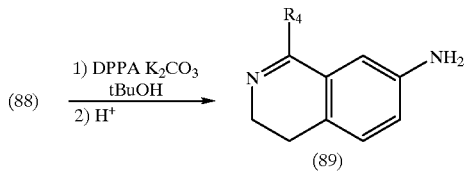
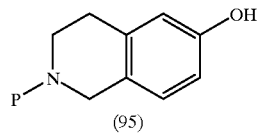

7-Substituted dihydroisoquinolines of general formula (84), (85), (88), and (89), wherein $R_4$ is as defined in formula 1, can be prepared as described in Scheme 13. Methoxy compounds of general formula (83), prepared as described in (Larsen, R. D., et al., JOC 56 (1991) 6034–6038), can be treated with boron tribromide to provide hydroxy compounds of general formula (84). Compounds of general formula (84) can be treated with a variety of halogenating reagents/systems such as triphenylphosphine/$Br_2$ or triphenylphosphine/$I_2$ to provide halogens of general formula (85), wherein X is Br or I. An alternative method of preparing iodides of general formula (85) can be used by converting dihydroisoquinolines of general formula (84) to triflates and then treating the triflates with magnesium iodide as described in (Martinez, G., et. al., Synthesis, (1986) N 3, 222–224). Dihydroisoquinolines (84) can be converted to methyl esters of general formula (87) via the triflate under conditions of carbon monoxide at 400 psi in the presence of a palladium catalyst in methanol. Methyl esters of general formula (87) can be treated with lithium hydroxide in a cosolvent of 1,4-dioxane and water to provide acids of general formula (88). Acids of general formula (88) can be treated under Curtius conditions as desribed in (Haefliger, W. and Kloppner, E., Helv. 65 (1982) 1837) or Schmidt conditions with hydrazoic acid as described in (Palmere, R. and Conley, R., JOC (1970) 2703) to provide amines of general formula (89).

Scheme 14

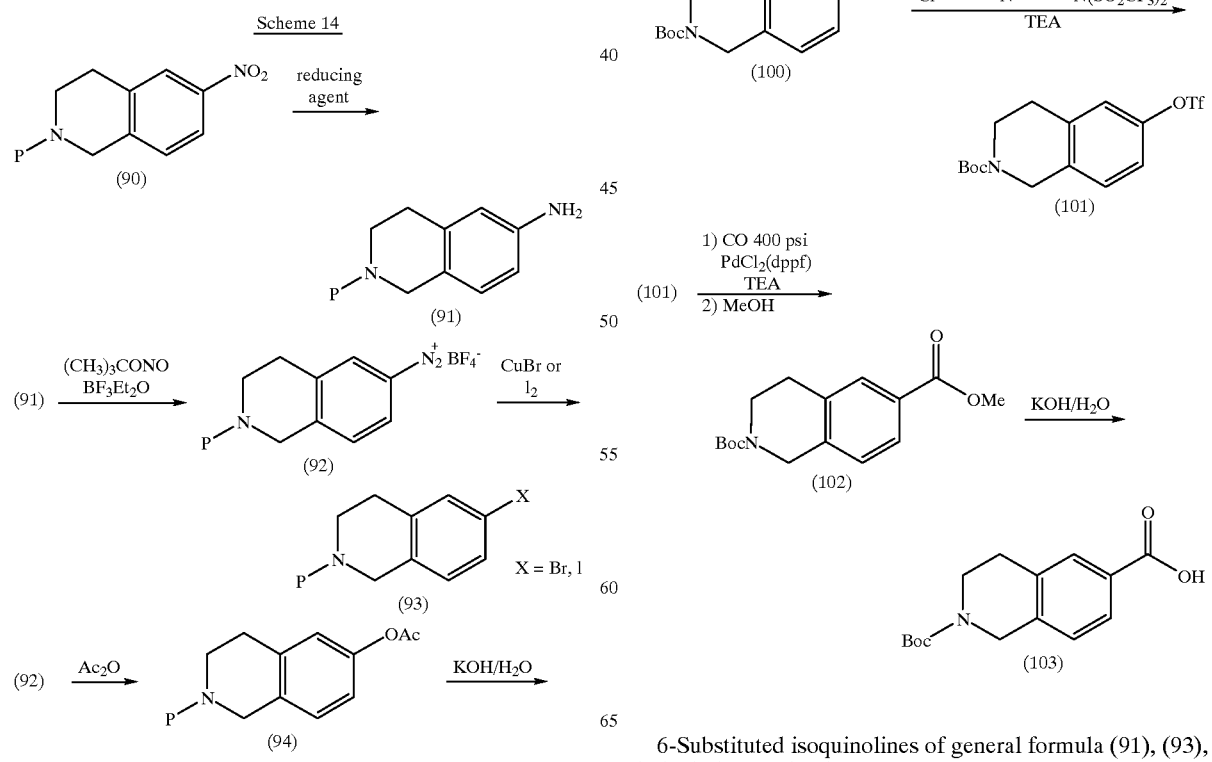

6-Substituted isoquinolines of general formula (91), (93), (95), (98), and (103), wherein P is hydrogen or a nitrogen protecting group, can be prepared as described in Scheme 14. Nitro compound (90), prepared as described in (Quallich, G. J., et al., JOC 63 (1998) 4116–4119), can be treated with a reducing agent such as iron powder in a cosolvent of acetic acid and water to provide amines of general formula (91). Amines of general formula (91) can be treated with t-butyl nitrite or sodium nitrite with boron triflouride etherate to provide diazonium compounds of general formula (92). Diazonium compounds of general formula (92) can be treated with cuprous bromide or iodide to provide halides of general formula (93) wherein X is Br or I. Diazonium compounds of general formula (92) can also be treated under similar conditions as described in (Koch, V. and Schnatterer S., Synthesis June (1990) 499–501) to provide acetates of general formula (94). Saponification of (94) provides hydroxy compounds of general formula (95). Hydroxy compounds of general formula (95) can also be prepared by treating methoxy compounds of general formula (96), prepared using a similar procedure as described in (Larsen, R. D., et al., JOC 56 (1991) 6034–6038; or Ajao, J. F. and Bird, C. W., J. Het. Chem. (1985) 329–331) with boron tribromide. An alternate method of preparing hydroxy compound (95), wherein P is hydrogen, can be used as described in (Selnick, H. G., Smith, G. R., Tebben, A. J., Syn. Comm. 25(20) (1995) 3255–3261). Nitrile compound (97), wherein P is t-butoxycarbonyl, can be prepared as described in (Selnick, H. G., Smith, G. R., Tebben, A. J., Syn. Comm. 25(20) (1995) 3255–3261). Nitriles of general formula (97) can be treated with aqueous sodium hydroxide solution in the presence of hydrogen peroxide to provide acids of general formula (98). An alternate method for preparing acid (103) can be used as desribed in Scheme 14. Hydroxy compound (99), after boc-protection (100), can be treated with 2-[N,N-bis(trifluoromethylsulfonyl)amino]-5-chloropyridine and a base such as TEA to provide compound (101). Triflate (101) can be treated with carbon monoxide at 400 psi in the presence of a palladium catalyst in a solvent such as methanol to provide methyl ester (102). Saponification of ester (102) provides acid (103).

Scheme 15

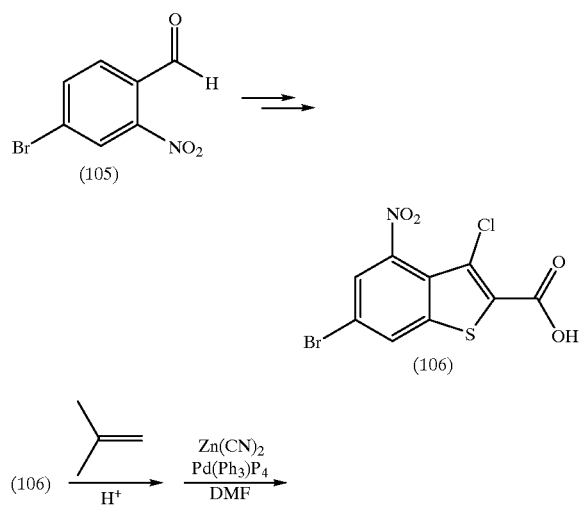

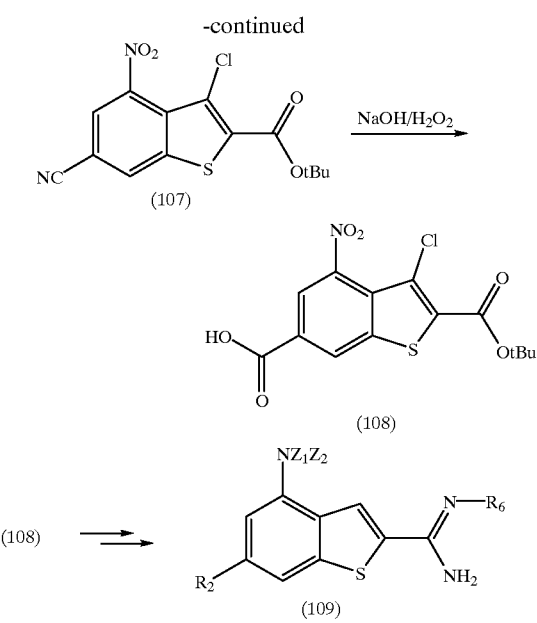

Disubstituted amidine benzothiophenes of general formula (109), wherein $Z_1$, $Z_2$, $R_2$, and $R_6$ are as defined in formula I, can be prepared as described in Scheme 15. 4-Bromo-2-nitrobenzaldehyde (105), prepared using the procedure described in (Voss, G. and Gerlach, H., Chem. Ber. 122(6) (1989) 1199–1201) can be transformed to 6-bromo-3-chloro-4-nitro-1-benzothiophene-2-carboxylic acid (106) following a similar procedure as that described in (Ried, W., Oremek, G., Ocakcioglu, B., Liebigs. Ann. Chem., 9 (1980) 1424–1427). 6-Bromo-3-chloro-4-nitro-1-benzothiophene-2-carboxylic acid (106) can be esterified with an acid/t-butanol system or a sulfuric acid/isobutylene system and then subjected to conditions as described in (Selnick, H. G., Smith, G. R., Tebben, A. J., Syn. Comm. 25(20) (1995) 3255–3261) to provide nitrile (107). Nitrile (107) can be treated with aqueous $NaOH/H_2O_2$ to provide acid (108). Acid (108) can be as desribed in Schemes 1–10 to provide disubstituted benzothiophenes of general formula (109).

The compounds and methods of the present invention will be better understood by reference to the following examples, which are intended as an illustration of and not a limitation upon the scope of the invention.

EXAMPLE 1

4-(2-pyrimidinylamino)-1-benzothiophene-2-carboximidamide, trifluoroacetic acid salt

EXAMPLE 1A

N-benzyl-3-fluoro-2-({[phenylmethyl]imino}methyl)aniline

A resealable tube was charged with 2,6-difluorobenzaldehyde (7.11 g, 50 mmol), benzylamine (27.3 mL, 250 mmol), cesium carbonate (19.5 g, 60 mmol), and dry toluene (170 mL). The tube was sealed and heated at 150° C. for 4 hours with rapid stirring. The reaction mixture was cooled and partitioned between ethyl acetate and 10% aqueous HCl. The organic layer was removed and the aqueous layer was extracted (2×, ethyl acetate). The combined organic extracts were washed (2×, saturated sodium bicarbonate; 2×, brine), dried (Na$_2$SO$_4$), filtered and concentrated under vacuum to provide the title compound (13.17 g; 83%) which was used without purification. MS (DCI/NH$_3$) m/e 318 (M+H)$^+$.

EXAMPLE 1B 2-(benzylamino)-6-fluorobenzaldehyde

To a solution of Example 1A (11.95 g, 3.9 mmol) in dioxane was added water (40 mL) until the solution just clouded and then dioxane was added until the solution became clear again(~5 mL). Oxalic acid (9.83 g, 78.0 mmol) was added in a single portion to give a dark orange solution which became a thick slurry. To the slurry was added in sequence: water (110 mL), dioxane (60 mL), and methanol (20 mL). This gave a mostly homogeneous solution with some small crystals which eventually dissolved as the reaction mixture was stirred for 1 hour. The volume of the reaction was reduced to ⅓ of the original volume by concentration under vacuum. The resulting solution was extracted (3×, ethyl acetate). The organic extracts were combined and washed (2×, 10% aqueous HCl; 2×, saturated aqueous NaHCO$_3$; 2×, brine), dried (Na$_2$SO$_4$), filtered and concentrated under vacuum to give a thick orange-yellow oil which was dried under vacuum at 45° C. to a constant weight providing the title compound (7.03 g, 79%) as a orange-yellow solid. This material was pure by $^1$H NMR. A small portion was recrystallized from ether/hexanes.

mp 72.5–74.5° C.;
MS (DCI/NH$_3$) m/e 230 (M+H)$^+$, 247 (M+NH$_4$)$^+$.

EXAMPLE 1C methyl 4-(benzylamino)-1-benzothiophene-2-carboxylate

To a solution of Example 1B (4.52 g, 19.7 mmol) in dry DMF (40 mL) was added, under a flow of nitrogen, methyl thioglycolate (2.91 mL, 32.5 mmol), and DBU (12.0 mL, 80.2 mmol). The reaction mixture was fitted with a septum (wired on), flushed with nitrogen, and heated at 70° C. until starting material was judged to be consumed by TLC (~1.5 hours). The reaction was cooled and partitioned between ethyl acetate and 10% aqueous HCl. The organic layer was removed and the aqueous layer was extracted (2×, ethyl acetate). The combined organic extracts were washed (3×, 10% aqueous HCl; 2×, saturated sodium bicarbonate; 2×, brine), dried (Na$_2$SO$_4$), filtered and concentrated under vacuum to give a chalky burnt orange solid. Trituration with ethyl acetate provided the title compound (1.7 g, 29%). The mother liquors were seeded with product to provide a second crop of the title compound which was collected by vacuum filtration (2.33 g, 40%).

mp 170–171° C.;
MS (DCI/NH$_3$) m/e 298 (M+H)$^+$, 315 (M+NH$_4$)$^+$.

EXAMPLE 1D methyl 4-amino-1-benzothiophene-2-carboxylate

Example 1C (1.0 g, 3.36 mmol) in THF:methanol:chloroform (40 mL: 10 mL: 10 mL) and 10% Pd/carbon (0.50 g) were combined and exposed to a hydrogen atmosphere via a hydrogen filled balloon. After 1 hour, TLC indicated that starting material was >98% consumed. The reaction mixture was flushed with nitrogen and filtered through a celite pad. The filter cake was thoroughly washed with THF (200 mL), chloroform (50 mL), and methanol (50 mL). The combined filtrates were concentrated under vacuum to give a yellow waxy solid which was purified on silica gel eluting with 500 mL of 20% ethyl acetate/hexanes then 30 % ethyl acetate/hexanes to provide the title compound as a yellow solid (0.58 g, 84%).

mp 145–146° C.;
MS (DCI/NH$_3$) m/e 208 (M+H)$^+$, 225 (M+NH$_4$)$^+$.

EXAMPLE 1E methyl 4-(2-pyrimidinylamino)-1-benzothiophene-2-carboxylate

A resealable vial was charged with a magnetic stirbar, Example 1D (0.11 g, 0.69 mmol), tris(dibenzylideneacetone) dipalladium(0) [Pd$_2$(dba)$_3$] (13.2 mg, 0.015 mmol), (S)-(−)-2,2'-bis(diphenylphosphino)-1,1'-binaphthyl (18.0 mg, 0.029 mmol), and toluene. The resulting solution was flushed with argon for 2 minutes and DBU (121 μL, 0.081 mmol) was added. The reaction vial was sealed and heated at 130° C. while monitoring by TLC. After 1.5 hours the reaction was removed from the oil bath and partitioned between water and ethyl acetate. The organic layer was drawn off and the aqueous layer was extracted with ethyl acetate (2×, ethyl acetate). The combined organic extracts were washed (2×, saturated sodium bicarbonate; 2×, brine), dried (Na$_2$SO$_4$), filtered, and concentrated under vacuum. Purification on silica gel, packed with dichloromethane, was accomplished by dissolving the residue in refluxing chloroform to load on the column; the column was eluted with increasing % ethyl acetate (2,4,6,10)/dichloromethane to provide the title compound as an off-white chalky solid (101.2 mg 61%). Recrystallization from ethyl acetate gave off-white crystals.

mp 206–208° C.
MS (DCI/NH$_3$) m/e 286 (M+H)$^+$.

EXAMPLE 1F 4-(2-pyrimidinylamino)-1-benzothiophene-2-carboximidamide, trifluoroacetic acid salt To a suspension of solid ammonium chloride (0.32, 5.93 mmol) in dry toluene (6 mL) at 0° C. was added a solution of 2.0 M trimethyl aluminum in toluene (3.0 mL, 5.93 mmol) at a rate which gave a steady evolution of gas. The cooling bath was removed and the reaction mixture was stirred at ambient temperature for 0.25 hours and transferred via syringe to a solution of Example 1D dissolved in the minimum volume of refluxing dry toluene (12 mL). A modest exotherm was noted during the addition process. The resulting solution was then incrementally heated until a vigorous exotherm was noted at 85–100° C. at which time the rate of heating was reduced. After the exotherm was complete, the reaction mixture was heated at reflux for 1.5 hours, cooled, and quenched by adding methanol (4.3 mL) and water (0.72 mL). The resulting solution was stirred for 1 hour and filtered through a paper filter on a buchner funnel. The filter cake was washed with hot methanol and the filtrate concentrated under vacuum to give a powdery yellow solid. Purification by reverse phase chromatography using a 0.1% trifluoroacetic acid in water and acetonitrile gradient provided the title compound (102.4 mg, 17%) after vacuum drying at 65° C. for 15 hours.

$^1$NMR (300 MHz, DMSO-d$_6$) δ 9.82 (br s; 1H), 9.44 (br s; 2H), 9.13 (br s; 2H), 8.60 (br s; 1H), 8.50 (d; 2H; J=5.0 Hz), 7.93 (d;1H; J=7.5 Hz), 7.87 (d; 1H; J=7.5 Hz), 7.57 (t; 1H; J=7.5,7.5 Hz), 6.92 (t; 1H; J=5.0,5.0 Hz);
MS (DCI/NH$_3$) m/e 270 (+H)$^+$;
Anal. calcd for C$_{13}$H$_{11}$N$_5$S(F$_3$CCO$_2$H)(0.5H$_2$O): C, 45.91; H, 3.33; N, 17.84. Found: C, 46.32; H, 3.15; N, 17.53.

EXAMPLE 2

4-(1,3-thiazol-2-ylamino)-1-benzothiophene-2-carboximidamide trifluoroacetic acid salt

EXAMPLE 2A methyl 4-[(aminocarbothioyl)amino]-1-benzothiophene-2-carboxylate

To a suspension of Example 1D (0.376 g, 1.82 mmol) in dry toluene (7 mL) was added thiophosgene (0.29 mL, 3.81 mmol) which resulted in a thick precipitate. THF (10 mL) was added and the slurry was heated at 100° C. until all of the precipitate dissolved. The reaction mixture was cooled and excess ammonium hydroxide was added to give an immediate precipitate. The solid was collected by vacuum filtration, rinsed with ethyl acetate, and dried under high vacuum to provide the title compound as a beige chalky solid (346.3 mg, 71%).

MS (DCI/NH$_3$) m/e 208 (M+H)$^+$, 225 (M+NH$_4$)$^+$.

EXAMPLE 2B methyl 4-(1,3-thiazol-2-ylamino)-1-benzothiophene-2-carboxylate

A solution of Example 2A (259 mg; 1.10 mmol) in iso-propanol (4.4 mL) in a resealable tube was treated with a 50% by weight aqueous solution of 2-chloroacetaldehyde (259 mg, 1.65 mmol). The tube was sealed and heated at 110° C. until all of the suspended solid dissolved (~2 hours). The volatiles were removed under vacuum and the resulting grayish solid was dried under high vacuum. Recrystallization from methanol/ethyl acetate gave the title compound as a flaky brown solid (130.1 mg). The mother liquors were purified on silica gel (packed in chloroform) by dissolving the residue in refluxing chloroform:acetone:methanol (2 mL:1 mL:0.5 mL). The column was eluted with dichloromethane to give the title compound as a light yellow chalky solid (159.7 mg). The combined yield was 289.8 mg (91%).

MS (DCI/NH$_3$) n/e 208 (M+H)$^+$, 225 (M+NH$_4$)$^+$.

EXAMPLE 2C 4-(1,3-thiazol-2-ylamino)-1-benzo[b]thiophene-2-carboximidamide tris(hydrochloric acid) salt Following the procedure from Example 1F but employing Example 2B in place of Example 1E provided the title compound after purification on silica gel using 5, 10, and 20% methanol/chloroform as the eluant and vacuum drying the resultant solid at 65° C. for 15 hours.

$^1$H NMR (300 MHz, DMSO-d$_6$) δ 9.53 (br s; 2H), 9.27 (br s; 2H), 8.78 (br s; 1H), 8.34 (d; 1H; J=7.5 Hz), 7.78 (d;1H; J=7.5 Hz), 7.56 (t; 1H; J=7.5,7.5 Hz), 7.33 (d; 1H; J=4.0 Hz), 7.04 (d; 1H; J=4.0 Hz);

MS (DCI/NH$_3$) m/e 275 (M+H)$^+$, 292 (M+NH$_4$)$^+$; Anal. calcd for C$_{12}$H$_{10}$N$_4$S$_2$(HCl)$_3$(H$_2$O)1.25: C, 35.08; H, 3.92; N, 13.62. Found: C, 34.99; H, 3.85; N, 13.38.

2-[amino(imino)methyl]-N-phenyl-1-benzothiophene-6-carboxamide

EXAMPLE 3A 2-(3-fluorophenyl)-1,3-dioxolane

A solution of 3-fluorobenzaldehyde (3.0 g, 24.2 mmol) in toluene (100 ml) was treated with ethylene glycol (1.8 g, 29.0 mmol) and p-toluenesulfonic acid (0.05 g, 0.24 mmol). The resulting solution was stirred at 80° C. for 3 hours. The reaction solution was partitioned between ethyl acetate and water. The organic layer was washed (brine), dried (Na$_2$SO$_4$), filtered, and concentrated under vacuum. The residue was purified on silica gel using 10% ethyl acetate/hexane to provide the title compound (3.4 g, 85%).

MS (DCI/NH$_3$) m/e 169 (M+H)$^+$.

EXAMPLE 3B

[2-(1,3-dioxolan-2-yl)-6-fluorophenyl](trimethyl)silane

A solution of diisopropylamine (0.34 g, 2.0 mmol) in dry THF (5 ml) was cooled to 0° C. and n-BuLi (0.88 mL of a 2.5M solution in hexane, 2.2 mmol) was added. The resulting solution was stirred for 10 minutes at 0° C. then cooled to −78° C. Example 3A in THF was added via syringe and the reaction mixture was stirred for 30 minutes followed by addition of chlorotrimethylsilane (0.33 g, 3.0 mmol) at −78° C. The reaction mixture was allowed to warm to ambient temperature and stirred another 10 minutes. The reaction mixture was partitioned between ethyl acetate and water. The organic layer was washed (brine), dried (Na$_2$SO$_4$), filtered, and concentrated under vacumm. The residue was purified on silica gel with 10% ethyl acetate/hexane to provide the title compound (0.23 g, 48%).

MS (DCI/NH$_3$) m/e 241 (M+H)$^+$.

EXAMPLE 3C 4-(1,3-dioxolan-2-yl)-2-fluoro-3-(trimethylsilyl)benzaldehyde

A solution of 2,2,6,6-tetramethylpiperidine (0.1 g, 0.42 mmol) in dry THF (3 ml) was cooled to 0° C. and treated with n-BuLi (0.25 mL of a 2.5M solution in hexane, 0.62 mmol). The resulting mixture was stirred for 10 minutes at 0° C. then cooled to −78° C. Example 3B in THF was added via syringe followed by addition of DMF (0.2 ml) with stirring for 3 hours. The reaction mixture was allowed to warm to ambient temperature and stirred another 10 minutes. The reaction mixture was partitioned between ethyl acetate and water. The organic layer was washed (brine), dried (Na$_2$SO$_4$), filtered, and concentrated under vacumm. The residue was purified on silica gel with 10% ethyl acetate/hexane to provide the title compound (0.07 g, 63%).

MS (DCI/NH$_3$) m/e 269 (M+H)$^+$.

EXAMPLE 3D methyl 6-(1,3-dioxolan-2-yl)-1-benzothiophene-2-carboxylate

A solution of Example 3C (1.0 g, 3.73 mmol) in dry DMF (30 ml) was treated with methyl thioglycolate (0.6 g, 5.6 mmol) and DBU (0.85 g, 5.6 mmol) under a nitrogen atmosphere. The resulting mixture was stirred for 3 hours at ambient temperature. The reaction mixture was partitioned between ethyl acetate and 10% HCl aqueous solution. The organic layer was washed (brine), dried (Na$_2$SO$_4$), filtered, and concentrated under vacumm. The residue was purified on silica gel with 25% ethyl acetate/hexane to provide the title compound (0.78 g, 80%).

MS (DCI/NH$_3$) m/e 265 (M+H)$^+$, 282 (M+NH$_4$)$^+$.

EXAMPLE 3E methyl 6-formyl-1-benzothiophene-2-carboxylate

A solution of Example 3D (0.78 g, 2.95 mmol) in acetone (10 ml) was treated with p-toluenesulfonic acid (0.03 g, 0.15 mmol). The resulting mixture was stirred for 1 hour at ambient temperature. The reaction mixture was partitioned between ethyl acetate and water. The organic layer was washed (brine), dried (Na$_2$SO$_4$), filtered, and concentrated under vacumm. The residue was purified on silica gel with 25% ethyl acetate/hexane to provide the title compound (0.64 g, 98%).

MS (DCI/NH$_3$) m/e 221 (M+H)$^+$.

EXAMPLE 3F 2-(methoxycarbonyl)-1-benzothiophene-6-carboxylic acid

A solution of Example 3E (0.62 g, 2.8 mmol) in acetonitrile (30 ml) was treated with sodium chlorite (0.36 g, 3.9 mmol) followed by H$_2$*$_2$ (10 ml, 30%). The resulting solution was stirred for 3 hours at ambient temperature. The reaction mixture was partitioned between ethyl acetate and water. The organic layer was washed (brine), dried (Na$_2$SO$_4$), filtered, and concentrated under vacumm. The residue was purified on silica gel with 50% ethyl acetate/hexane to provide the title compound (0.58 g, 87%). MS (DCI/NH$_3$) m/e 237 (M+H)$^+$.

EXAMPLE 3G methyl 6-(anilinocarbonyl)-1-benzothiophene-2-carboxylate

A suspension of Example 3F (0.3 g, 1.3 mmol) in CH$_2$Cl$_2$ (50 ml), was treated with oxalyl chloride (0.64 g, 5.1 mmol) followed by addition of two drops of dry DMF. The resulting mixture was refluxed 1 hour and concentrated under vacuum to provide the acid chloride which was used without purification.

A solution of the acid chloride in CH$_2$Cl$_2$ (30 ml) was treated with aniline (0.23 g, 2.5 mmol) and triethylamine (0.25 g, 2.5 mmol). The resulting mixture was stirred at ambient temperature for 2 hours. The reaction mixture was partitioned between ethyl acetate and 10% HCl aqueous solution. The organic layer was washed (brine), dried (Na$_2$SO$_4$), filtered, and concentrated under vacumm. The residue was purified on silica gel with 20% ethyl acetate/CH$_2$Cl$_2$ to provide the title compound (0.2 g, 51%).

MS (DCI/NH$_3$) m/e 312 (M+H)$^+$, 329 (M+NH$_4$)$^+$.

EXAMPLE 3H

2-[amino(imino)methyl]-N-phenyl-1-benzothiophene-6-carboxamide

Example 3G was processed according to the procedure described in Example 1F. The residue was purified on silica gel with 25% methanol/chloroform to provide the title compound (0.12 g, 57%).

$^1$H NMR (300 MHz, DMSO-d$_6$) δ 10.53 (s; 1H), 9.60 (br s; 3H), 8.84 (s; 1H), 8.51 (s; 1H), 8.19 (d; 1H; J=8.5 Hz), 8.09 (d, 1H, J=8.5 Hz), 7.84 (d; 2H; J=8.5 Hz), 7.38 (t; 2H; J=8.5 Hz), 7.14 (t; 1H; J=8.5 Hz);

MS (DCI/NH$_3$) m/e 296 (M+H)$^+$;

Anal. calcd for C$_{16}$H$_{13}$N$_3$OS (HCl): C, 57.91; H, 4.25; N, 12.66. Found: C, 51.91; H, 4.39; N, 11.08.

2-[amino(imino)methyl]-N-(3-isopropoxyphenyl)-1-benzothiophene-6-carboxamide

EXAMPLE 4

EXAMPLE 4A methyl 6-[(3-isopropoxyanilino)carbonyl]-1-benzothiophene-2-carboxylate Example 3F was processed according to the procedure described in Example 3G substituting 3-isopropoxyaniline for aniline. The residue was purified on silica gel with 10% ethyl acetatel/CH$_2$Cl$_2$ to provide the title compound (0.31 g, 69%).

MS (DCI/NH$_3$) m/e 397 (M+H)$^+$.

EXAMPLE 4B

2-[amino(imino)methyl]-N-(3-isopropoxyphenyl)-1-benzothiophene-6-carboxamide

Example 4A was processed according to the procedure described in Example 1F. The residue was purified on silica gel with 25% methanol/chloroform to provide the title compound (0.18 g, 57%).

$^1$H NMR (300 MHz, DMSO-d$_6$) δ 10.42 (s; 1H), 9.50 (br s; 3H), 8.80 (s; 1H), 8.47 (s; 1H), 8.19 (d; 1H; J=8.5 Hz), 8.07 (d, 1H, J=8.5 Hz), 7.49 (s; 1H), 7.38 (d; 1H; J=8.5 Hz), 7.24 (t; 1H; J=8.5 Hz), 6.69 (d; 1H, J=8.5 Hz), 4.58 (m; 1H), 1.29 (d; 6H; J=6.0 Hz);

MS (DCI/NH$_3$) m/e 354 (M+H)$^+$;

Anal. calcd for C$_{19}$H$_{19}$N$_3$O$_2$S (HCl): C, 58.53; H, 5.17; N, 10.78. Found: C, 55.47; H, 5.26; N, 10.10.

What is claimed is:

1. A compound of formula II:

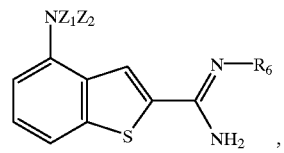

II or a pharmaceutically acceptable salt or prodrug thereof, wherein

Z$_1$ is a heterocycle selected from the group consisting of pyrimidinyl, pyrazinyl, piperazinyl morpholinyl, tetrazinyl and pyridazinyl;

Z$_2$ is selected from hydrogen and alkyl; and

R$_6$ is selected from hydrogen and hydroxy.

2. A compound according to claim 1 wherein Z$_1$ is pyrimidinyl.

3. A compound according to claim 2 which is 4-(2-pyrimidinylamino)-1-benzothiophene-2-carboximidamide.

4. A composition for inhibiting urokinase comprising both a pharmaceutical carrier and a therapeutically effective amount of a compound of claim 1.

5. A method for inhibiting urokinase in a mammal in need of such treatment, comprising adminstering to the mammal a therapeutically effective amount of a compound of claim 1.

* * * * *